(12) United States Patent
Ray

(10) Patent No.: US 9,999,478 B1
(45) Date of Patent: Jun. 19, 2018

(54) ANESTHETIC CABLE PROTECTOR

(71) Applicant: Sheila Barrett Ray, Harrisburg, MO (US)

(72) Inventor: Sheila Barrett Ray, Harrisburg, MO (US)

( * ) Notice: Subject to any disclaimer, the term of this patent is extended or adjusted under 35 U.S.C. 154(b) by 0 days. days.

(21) Appl. No.: 15/472,133

(22) Filed: Mar. 28, 2017

(51) Int. Cl.
  *A61B 50/20* (2016.01)
  *A61M 16/08* (2006.01)
  *B65D 43/16* (2006.01)
  *B65D 43/22* (2006.01)

(52) U.S. Cl.
  CPC ......... *A61B 50/20* (2016.02); *A61M 16/0875* (2013.01); *B65D 43/16* (2013.01); *B65D 43/22* (2013.01); *A61M 2209/082* (2013.01)

(58) Field of Classification Search
  CPC ...................................................... A61B 50/20
  USPC ...................................................... 174/68.3
  See application file for complete search history.

(56) References Cited

U.S. PATENT DOCUMENTS

| 4,114,241 A | 9/1978 | Bisping | |
| 7,301,101 B2 * | 11/2007 | Suzuki | H02G 3/30 174/117 F |
| 8,546,694 B1 * | 10/2013 | Harrison | B65H 75/362 174/135 |

FOREIGN PATENT DOCUMENTS

CN          104189981 A     12/2014

* cited by examiner

*Primary Examiner* — Hoa C Nguyen
*Assistant Examiner* — Stanley Tso
(74) *Attorney, Agent, or Firm* — Benesch, Friedlander, Coplan & Aronoff LLP

(57) ABSTRACT

A medical safety device for holding and protecting medical circuitry connected between a medical patient and medical equipment is provided. The device can include an outer shell with an exterior sidewall and an interior sidewall defining an open interior. The outer shell can include a door that can be opened to allow access to the interior of the shell. The outer shell can include at least one latch for selectively securing the door in a closed position. The exterior shell can include connecting components for connecting the device to a hospital or surgical bed frame. The interior of the outer shell can include a grooved section having one or more grooves. The grooves can be configured to hold and retain different types of medical circuitry, such as cords, wires, tubes and the like.

14 Claims, 9 Drawing Sheets

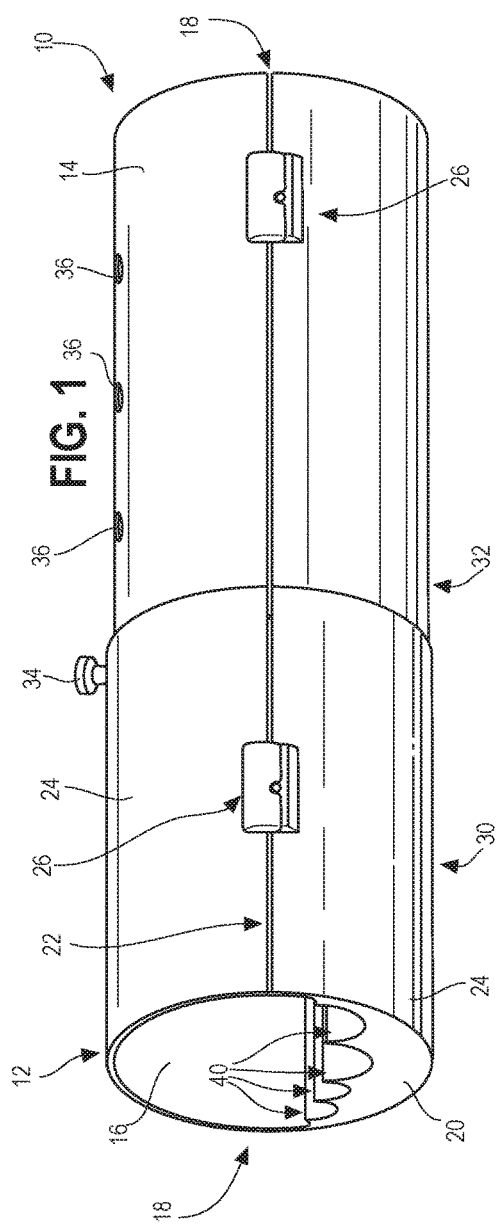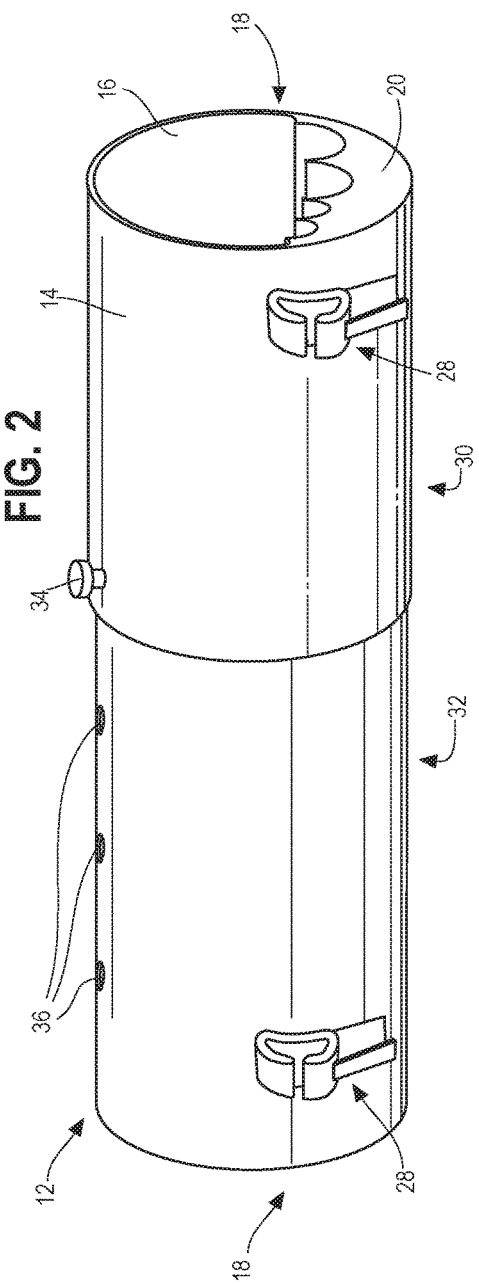

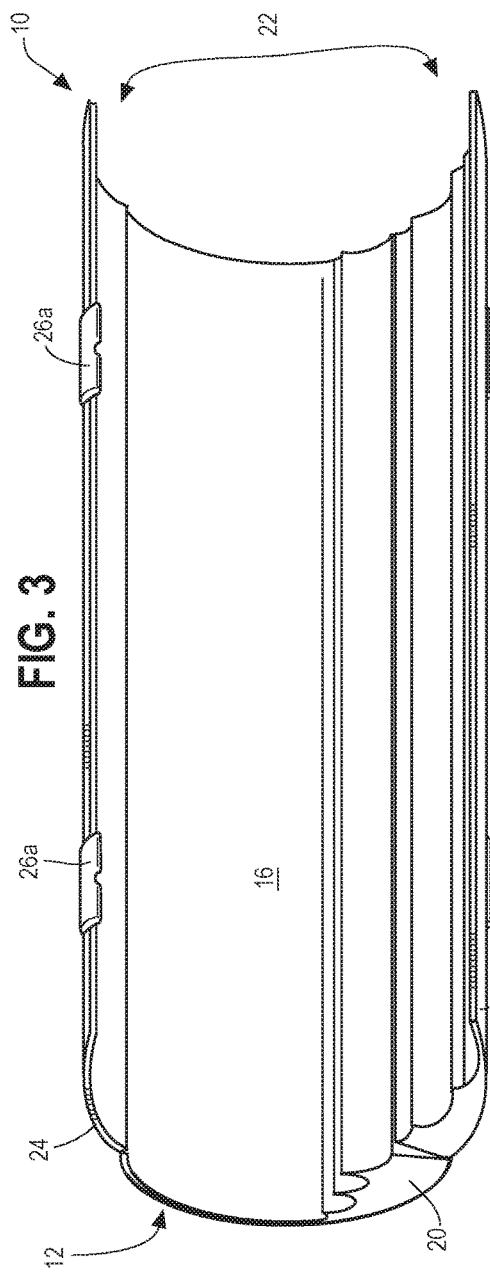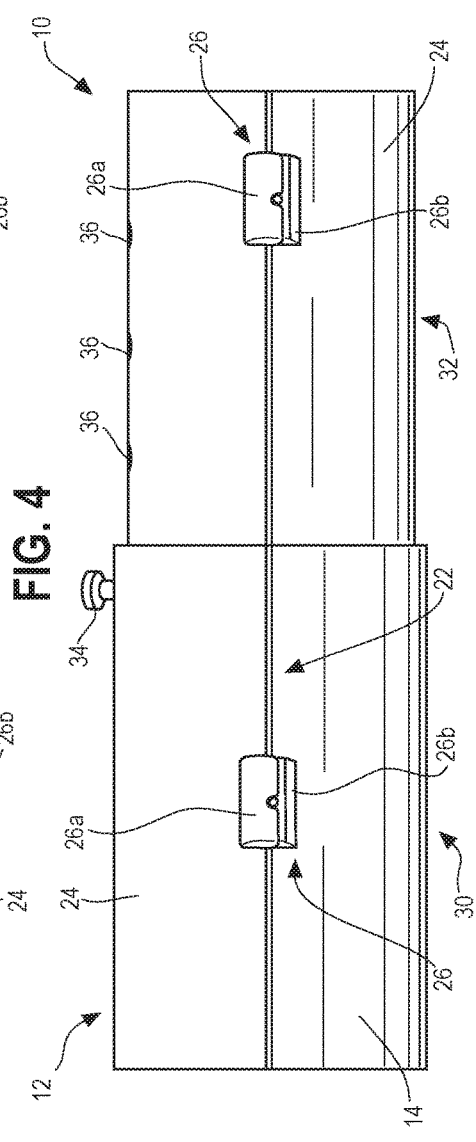

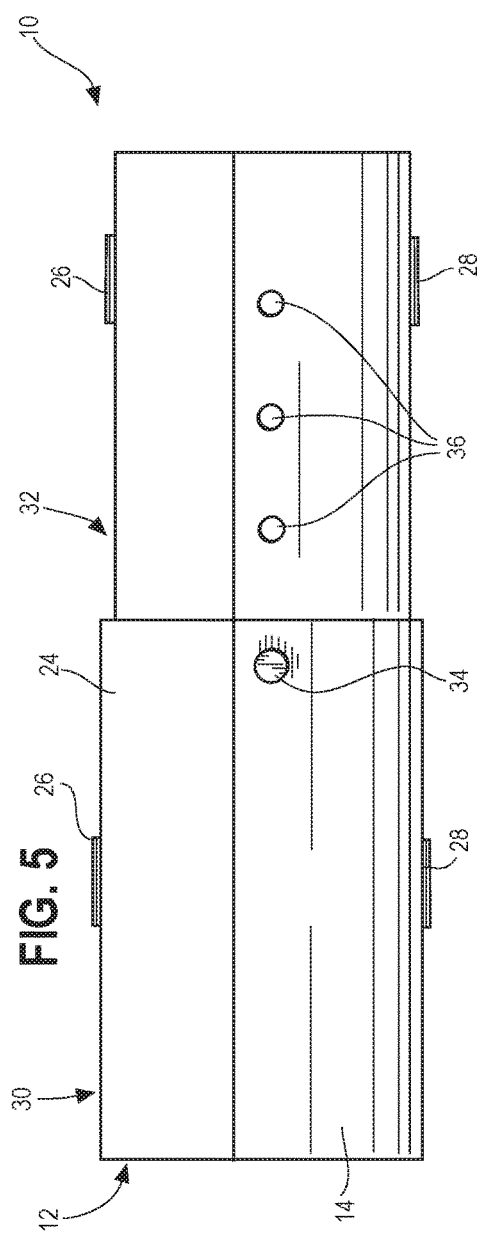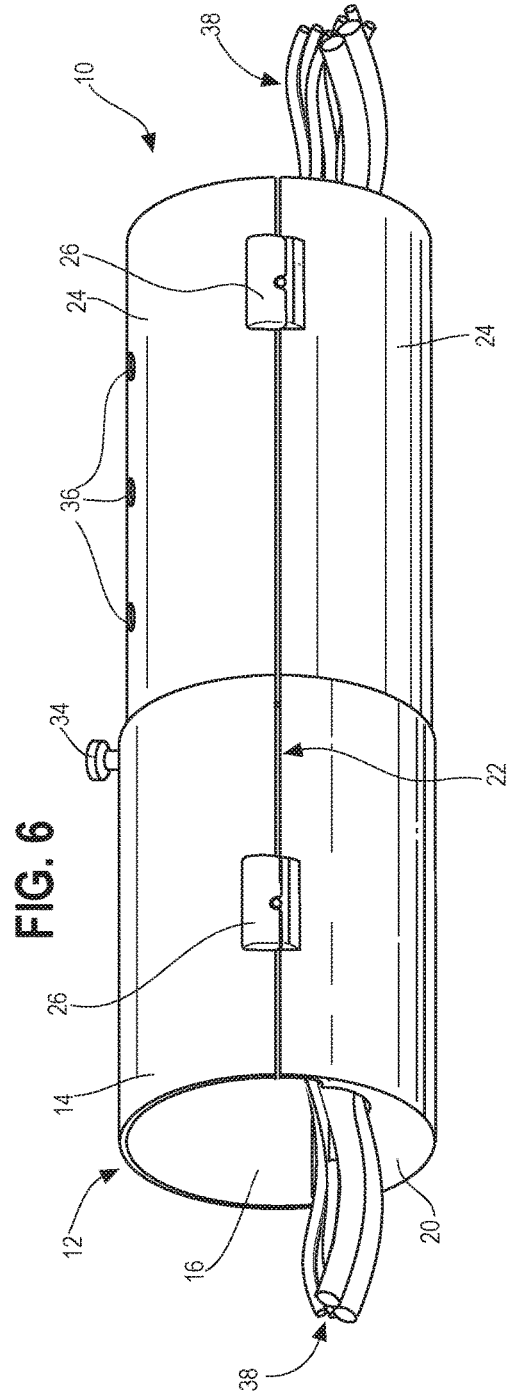

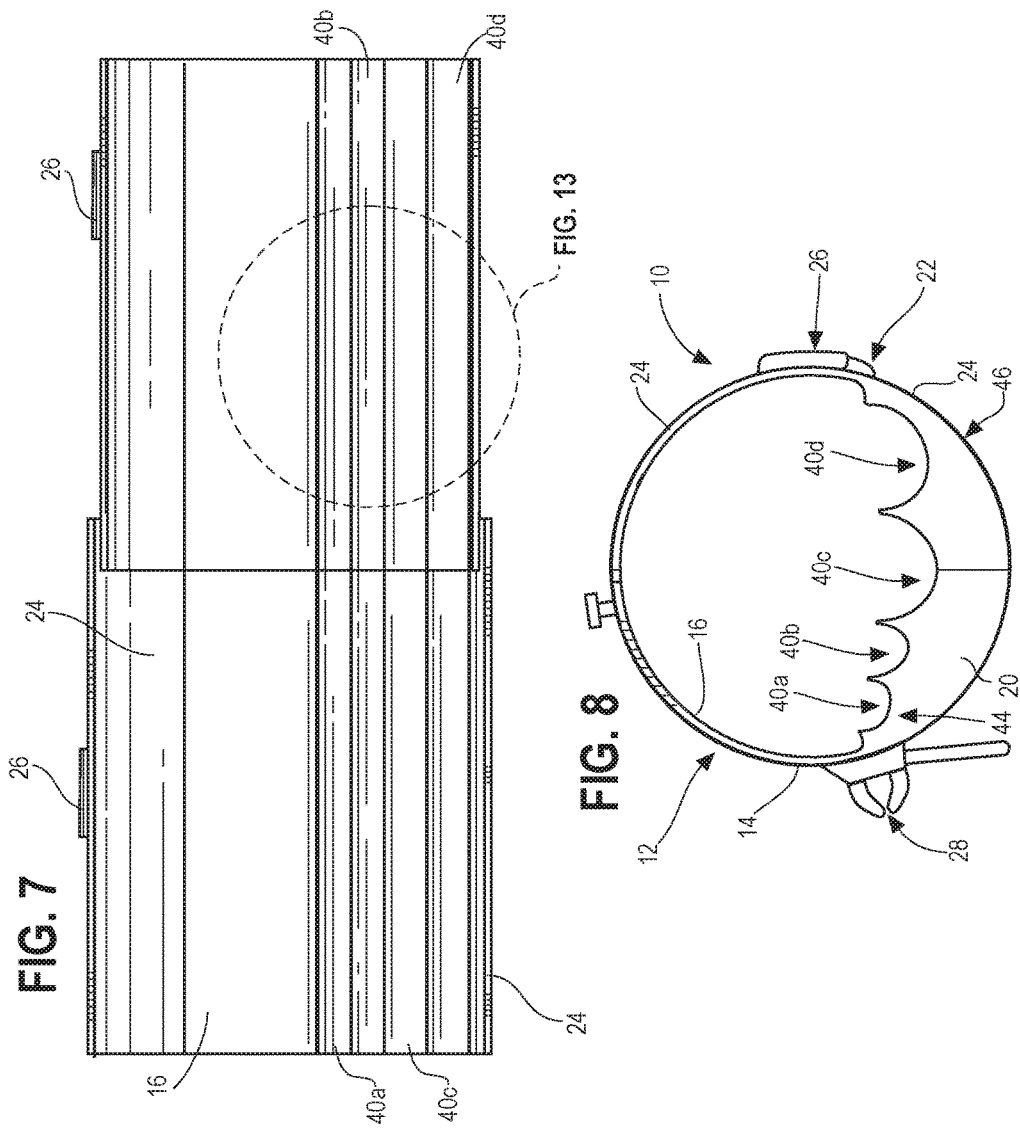

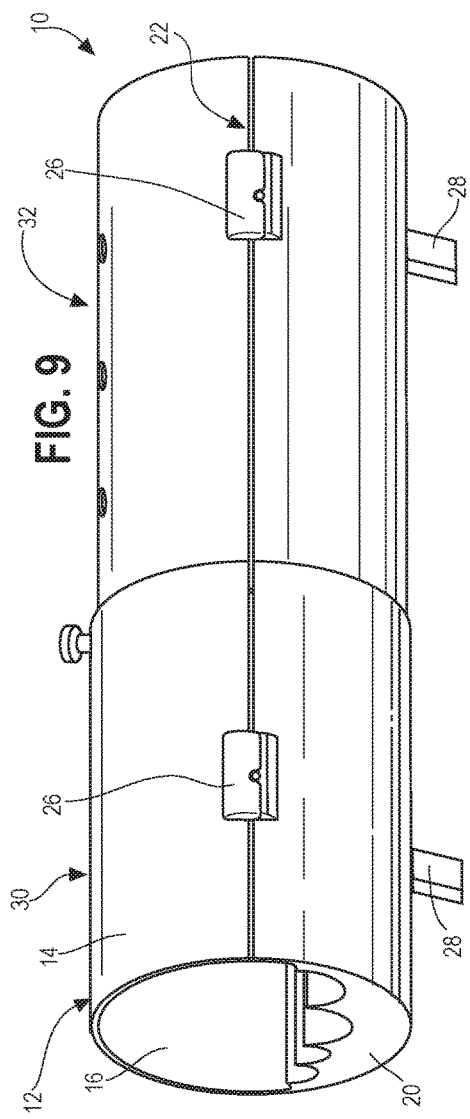
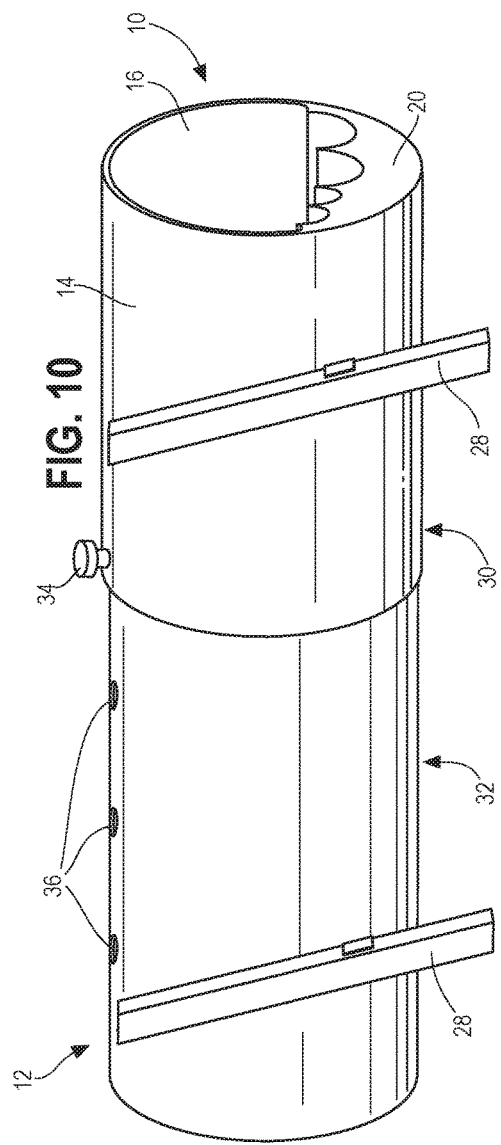

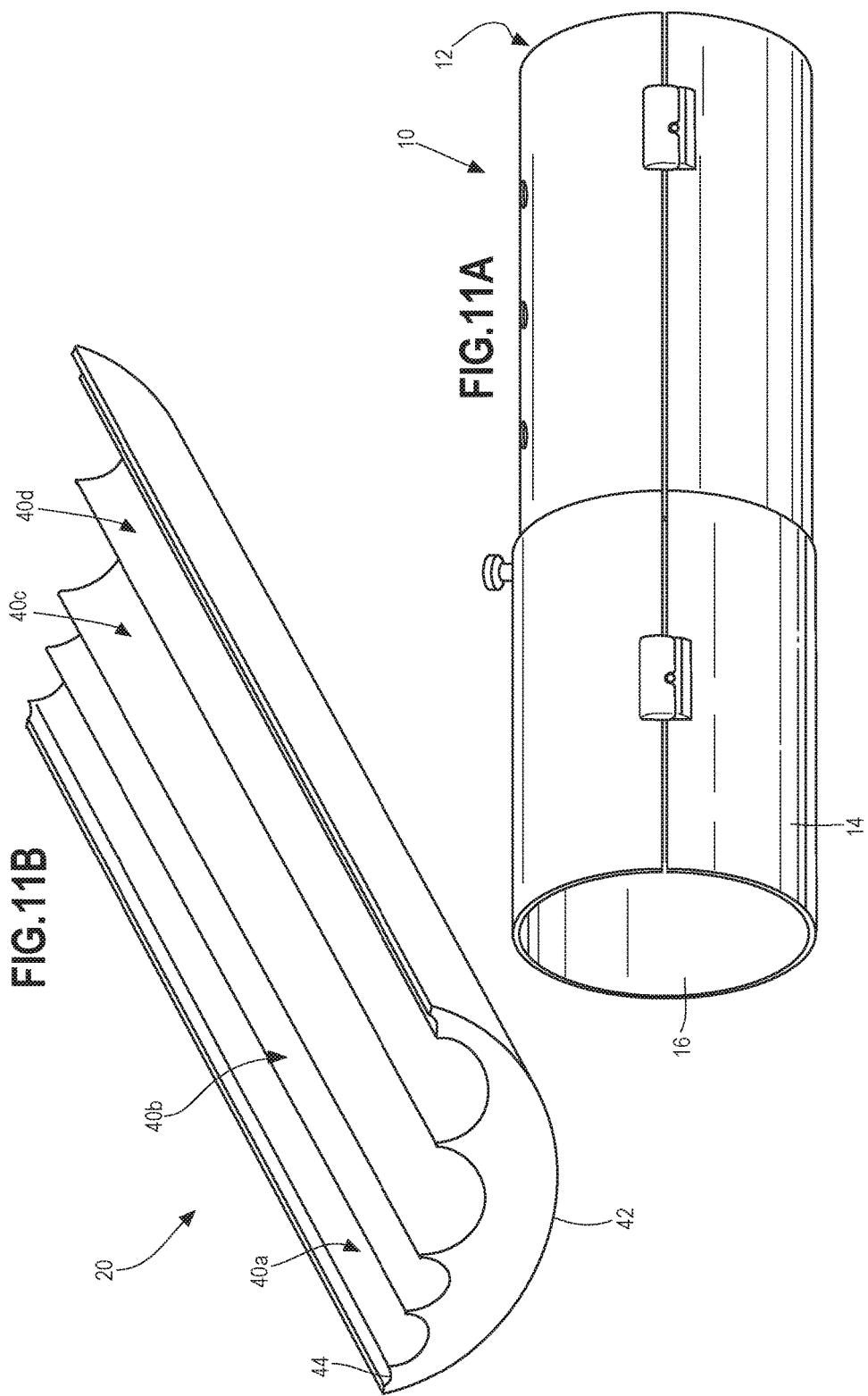

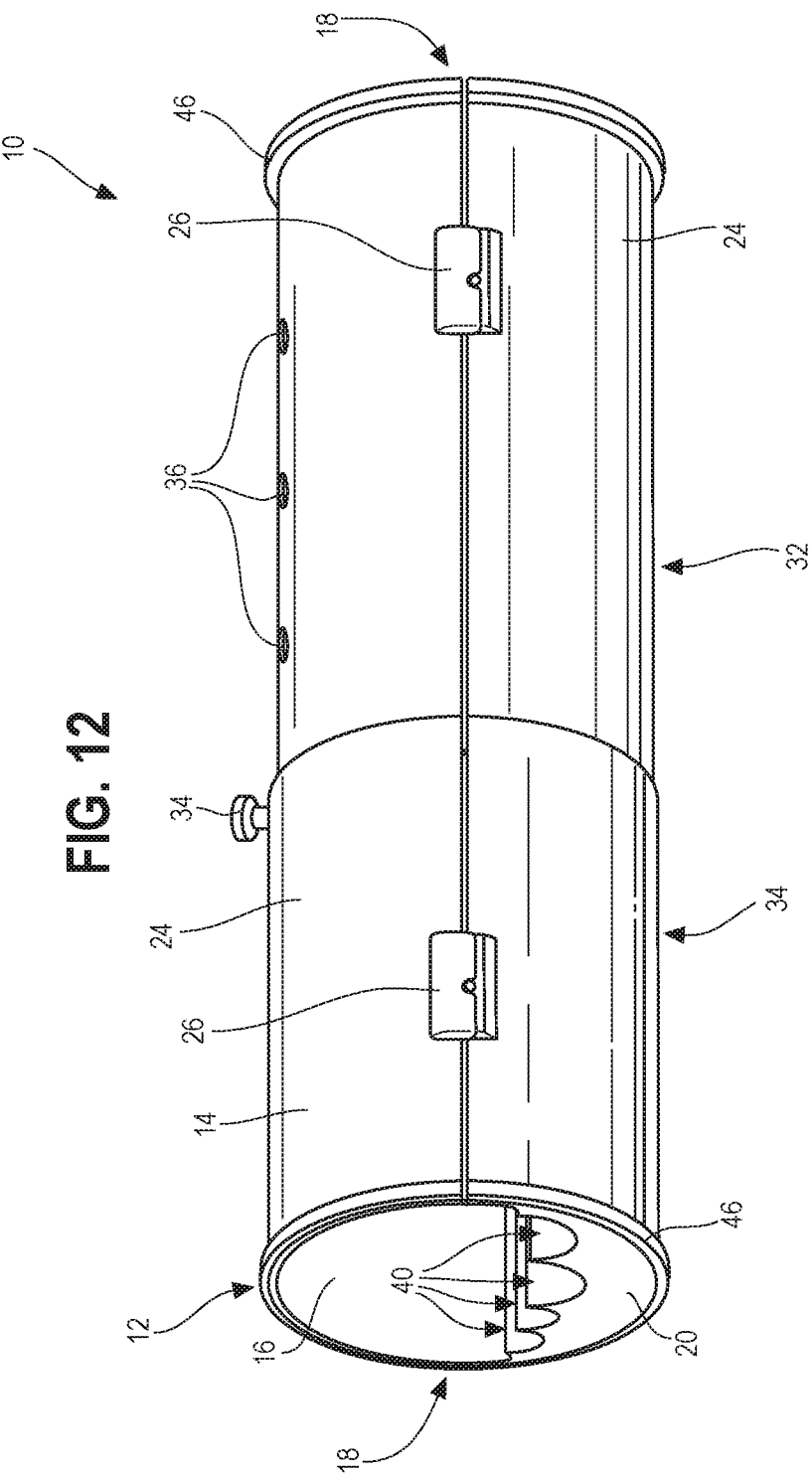

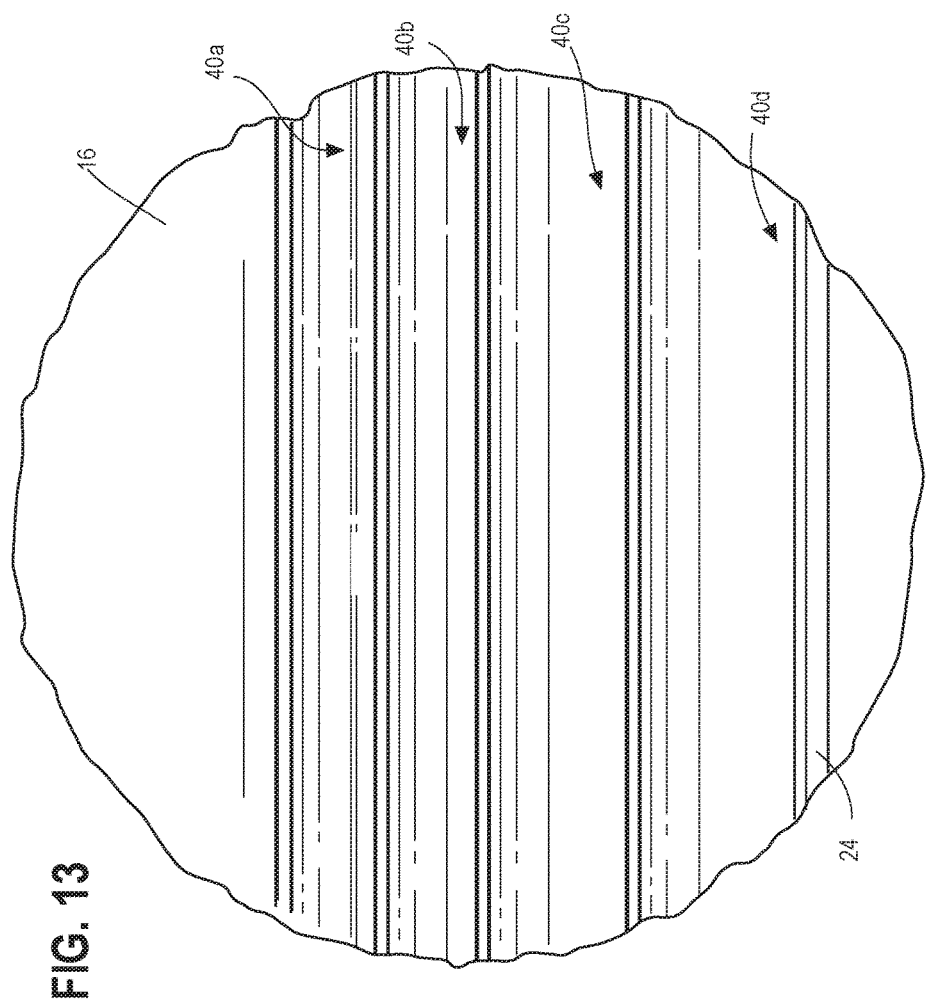

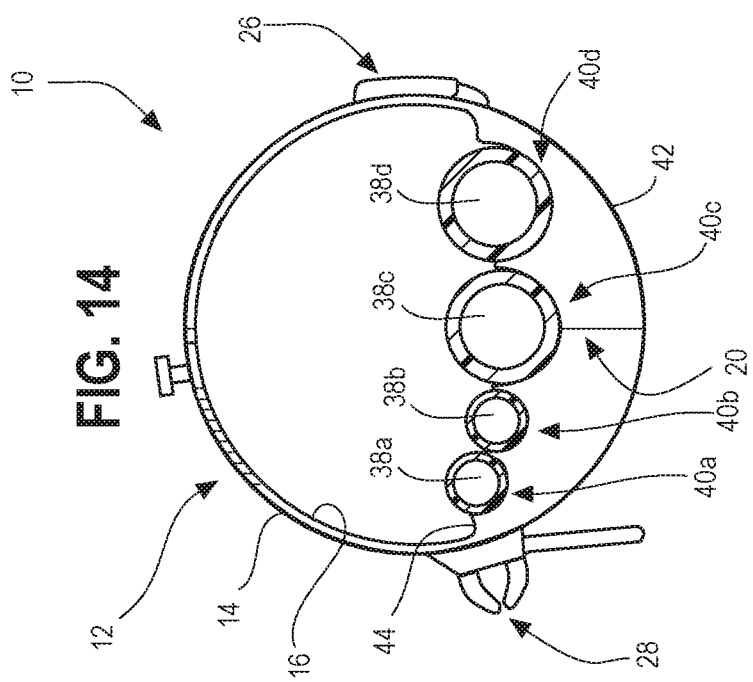

ANESTHETIC CABLE PROTECTOR

CROSS-REFERENCE TO RELATED APPLICATIONS

None.

FIELD OF THE INVENTION

The present invention relates generally to a protecting device for holding and protecting cables and circuits, and in particular, a device for protecting cables and circuits associated with anesthetic and other medical equipment connected to patients.

BACKGROUND OF THE INVENTION

Medical patients commonly need to be connected to one or more types of medical devices and equipment when placed in a hospital bed or during surgery. The medical devices and equipment is generally connected to the patient via medical circuitry (e.g., cords, tubes, wires, and the like). For example, medical patients must often times be hooked up to IV lines, EKG, pulse oximetry, electrocardiogram, non-invasive and invasive blood pressure, temperature cords, other monitoring wires or cables, and inspiratory and/or expiratory anesthesia tubing. In current practice, the medical circuitry (e.g., anesthesia tubing, medical cables, etc.) connected between the patient and the various medical devices and equipment are not protected or enclosed to reduce the incidence of damage and disconnection from the patient. This can result in the medical circuitry becoming easily tangled, kinked and/or disconnected with movement around the hospital or surgical bed and/or rotation of the bed itself, such as during a surgical procedure. Doctors, surgeons, nurses and other medical personnel also commonly stand on the same side of the hospital or surgical bed in which the medical circuitry is located further increasing the chance of an accidental disconnection from the patient.

The accidental interference and/or disconnection with the medical circuitry can impose severe complications for the patient and surgical procedures. For example, extubation of the endotracheal tube can create issues of difficult laryngoscopy and can result in hypoxia, cardiac arrest and even death.

Accordingly, a need exists for a safety device that can secure medical circuitry connected to medical patients and reduce the likelihood of accidental interference with such medical circuitry while the patient is in a hospital bed or undergoing surgery.

SUMMARY OF THE INVENTION

The present invention is directed generally to a medical safety device for protecting medical circuitry connecting a patient to medical devices and equipment. Medical circuitry can include inspiratory and expiratory anesthesia tubing, EKG and pulse oximetry cords, temperature wires, blood pressure monitors, and any number of different types of medical or non-medical circuitry, including cords, cables, wires, tubing, and the like. According to an exemplary embodiment of the present invention, the medical safety device can comprise an elongated hollow cylindrical tube having an exterior sidewall and an interior sidewall. The medical safety device can further include an opening defined through each end of the cylindrical tube to allow the medical circuitry to extend continuously through the medical safety device. The medical safety device can further include a door provided on the cylindrical tube that can be selectively opened and closed to allow access to the interior of the cylindrical tube. The medical safety device can include at least one latch provided on the exterior sidewall that can be configured to selectively secure the door in a closed position. The medical safety device can include a grooved section extending along the interior sidewall, where the grooved section includes a plurality of circuit grooves configured for holding and securing one or more medical circuits within the cylindrical tube. The medical safety device can further include a securing component on the exterior sidewall of the cylindrical tube that can be configured to selectively secure the medical safety device to an object, such as a hospital or surgical bed frame.

According to one embodiment of the present invention, the medical safety device can include a first shell section and a second shell section slidably receivable within the first shell section. Collectively, the first and second shell sections can form the elongated hollow cylindrical tube. The second shell section can be configured to slide into and out of the first shell section in order to allow the length of the medical safety device to be adjusted. In order to secure the first and second shell sections together at a desired length, the first shell section can include a fastener and the second shell section can include a plurality of spaced apart openings that can be aligned with the fastener, which can be inserted into the opening to secure the first and second shell sections together.

According to an exemplary embodiment of the present invention, the grooved section of the medical safety device can be configured as a removable mold that can be removed from and inserted into the interior of the cylindrical tube.

According to an exemplary embodiment of the present invention, the grooved section of the medical safety device can include a set of primary grooves and a set of secondary grooves, where the primary grooves are larger than the secondary grooves.

Other aspects and advantages of the present invention will be apparent from the following detailed description of the preferred embodiments and the accompanying drawing figures.

DESCRIPTION OF THE SEVERAL VIEWS OF THE DRAWING

In the accompanying drawing, which forms a part of the specification and is to be read in conjunction therewith in which like reference numerals are used to indicate like or similar parts in the various views:

FIG. 1 is a front perspective view of a medical safety device for holding medical circuitry connected between a patient and medical devices and equipment in accordance with one embodiment of the present invention;

FIG. 2 is a rear perspective view of the medical safety device of FIG. 1;

FIG. 3 is a front perspective view of the medical safety device of FIG. 1 illustrating the medical safety device in an open configuration in accordance with one embodiment of the present invention;

FIG. 4 is a front elevation view of the medical safety device of FIG. 1;

FIG. 5 is a top plan view of the medical safety device of FIG. 1;

FIG. 6 is a front perspective view of a medical safety device holding medical circuitry that can be connected between a patient and medical devices and equipment in accordance with one embodiment of the present invention;

FIG. 7 is a top plan view of a medical safety device in an open configuration to illustrate the location of grooves for holding medical circuitry within the interior of the medical safety device in accordance with one embodiment of the present invention;

FIG. 8 is an end elevation view of the medical safety device of FIG. 1;

FIG. 9 is a front perspective view of a medical safety device for holding medical circuitry connected between a patient and medical devices and equipment in accordance with another embodiment of the present invention;

FIG. 10 is a rear perspective view of the medical safety device of FIG. 9;

FIGS. 11A and 11B are front perspective views of a medical safety device for holding medical circuitry connected between a patient and medical devices and equipment and a grooved section mold for insertion into the interior of the medical safety device in accordance with another embodiment of the present invention;

FIG. 12 is a front perspective view of a medical safety device for holding medical circuitry connected between a patient and medical devices and equipment in accordance with another embodiment of the present invention;

FIG. 13 is an enlarged partial view of the grooves on the interior of the medical safety device shown in FIG. 7; and FIG. 14 is an end elevation view of the medical safety device of FIG. 8 illustrating medical circuitry located in each of the grooves defined in the interior of the medical safety device in accordance with one embodiment of the present invention.

DETAILED DESCRIPTION OF THE INVENTION

The invention will now be described with reference to the drawing figures, in which like reference numerals refer to like parts throughout. For purposes of clarity in illustrating the characteristics of the present invention, proportional relationships of the elements have not necessarily been maintained in the drawing figures.

The following detailed description of the invention references specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The present invention is defined by the appended claims and the description is, therefore, not to be taken in a limiting sense and shall not limit the scope of equivalents to which such claims are entitled.

The present invention is directed toward a medical circuit protecting device 10 that can be used to protect and secure medical circuiting connecting a medical patient to various types of medical equipment, devices, monitoring systems and treatments. For example, device 10 can be used as a anesthesia safety protection device that holds and secures inspiratory and expiratory anesthesia tubing, along with other monitoring or medical circuitry (e.g., EKG and pulse oximetry cords, temperature wires, blood pressure monitors, etc.), connected to a patient. It is also recognized that device 10 can be configured for holding any number of different types of medical or non-medical circuitry, including cords, cables, wires, tubing, and the like (referred to herein as "circuits") connected between a patient and various medical monitoring and provisioning equipment. Device 10 also can be configured to secure the medical circuitry contained therein against a hospital or surgical bed frame or other object to prevent the circuits from becoming entangled or kinked and to prevent the accidental disconnection of the circuits from medical equipment or the patient.

For example, during surgical procedures, particularly robotic surgeries, medical circuitry connected between machines and equipment and a medical patient can easily become tangled and even disconnected during surgery due to rotation of the surgical bed and/or maneuvering of various equipment, surgeons and assistants. Device 10 can be utilized to keep the medical circuitry secured closely to the surgical bed in order to prevent such entanglement and disconnection. In addition, medical circuitry connected to a patient can often hang down near the legs and feet of doctors, surgeons, nurses, assistants, medical staff, guests, family members, or other persons positioned in close proximity to the patient's bed. As a result, the medical circuitry is susceptible to becoming caught in the legs and feet of such persons moving nearby the patient bed resulting in the medical circuitry becoming disconnected from the medical equipment or machines and the patient, which can compromise the status of the patient. Device 10 can be used to keep the medical circuitry closely secured to the patient bed to prevent such accidents.

Turning to the figures, device 10 can comprise an outer shell 12 in the form of a cylindrical tube with a hollow interior that can receive various medical circuitry. Outer shell 12 can include an exterior sidewall 14 and an interior sidewall 16 that can define the interior portion of device 10. Extending through the ends of shell 12 can be openings 18 that can enable the medical circuitry to extend through and be contained within device 10 without interruption. Positioned within the interior portion of device 10 and on a portion of interior sidewall 16 can be a grooved section 20 that can be configured with a plurality of grooves suitable for receiving and holding medical circuitry of various sizes and dimensions. According to one exemplary embodiment of device 10, grooved section 20 is defined into interior sidewall 16 of device 10 (see FIGS. 1 and 2). According to another exemplary embodiment, grooved section 20 is configured as a mold that can be removable from shell 12, as described in greater detail below (see FIGS. 11A and 11B).

According to an exemplary embodiment of the present invention, shell 12 can include a door 22 that can be moved between an open position (FIG. 3) and a closed position (FIG. 4) in order to allow access to the interior portion of device 10. According to one exemplary embodiment, door 22 can be configured as a pair of pivotally connected door panels 24 that open in opposing directions about hinge lines in order to provide access to the interior of device 10. It is also recognized that in alternative embodiments, door 22 can alternatively be configured as a sliding door, a removable door panel, or other suitable design for allowing selective access to the interior portion of device 10. To keep door 22 in a closed position and allow for selective access to the interior portion of device 10, device 10 can include one or more latches 26 provided on exterior sidewall 14 of shell 12. Each latch 26 can be constructed as any suitable type of latch, clip, clamp, clasp, lock, fastener, or other suitable type of closure means. According to one exemplary embodiment, latch 26 includes a first locking portion 26a hingedly connected to one door panel 24 and a second receiving portion 26b provided on the other door panel 24 (see FIG. 4), where the first locking portion 26a can be pressed and selectively locked onto the second receiving portion 26b in order to secure door panels 24 in a closed position with respect to exterior sidewall 14.

According to an exemplary embodiment of the present invention, device 10 can include one or more securement means 28 configured to selectively and releasably attach device 10 to an object, such as but not limited to a surgical bed frame, a hospital bed frame, a patient chair, or a wheel chair. According to one exemplary embodiment, securement means 28 can be configured as a quick release clamp, such as those known in the hospital and medical care industry, and designed to quickly and easily attached to part of a hospital bed frame (see FIG. 2). According to another exemplary embodiment, securement means 28 can be configured as an elongated vertical bar or rod configured to be received by a locking clamp located on a hospital bed frame as commonly known in the industry (see FIG. 10). It is also recognized that securement means 28 can be configured as any suitable type of lock, latch, clamp, clip or other suitable type of locking components known in the art.

According to one exemplary embodiment of the present invention, outer shell 12 can include a first shell section 30 and a second shell section 32 (see FIGS. 1 and 2). Second shell section 32 can be configured to be slidably receivable within first shell section 30 and can allow device 10 to have a selectively adjustable length. For example, according to one exemplary embodiment, device 10 can have an adjustable length between 24 inches and 38 inches; however, it is recognized that device 10 can just as suitably be configured with any number of other suitable dimensions. Both shell sections 30 and 32 can be formed together into outer shell 12 by maintaining an overlapping region between the two shell sections 30 and 32. In order to allow second shell section 32 to be slidably received within first shell section 30, second shell section 32 can be configured with an exterior diameter and slightly less than the interior diameter of first shell section 30. In addition, the interior sidewalls 16 and grooved sections 20 of each shell section 30 and 32 can be configured to allow exterior sidewall 14 of second shell section 32 to slide under grooved section 20 of first shell section 30 so that second shell section 32 is not obstructed by the shape of the interior sidewall 16 of first shell section 30.

Device 10 can be configured with a shell section fastener 34 and one or more fastener openings 36 in order to allow device 10 to be selectively adjusted to various lengths by adjusting the length of the overlapping region between first shell section 30 and second shell section 32. According to one exemplary embodiment, first shell section 30 includes fastener 34, which can be any type of suitable fastener extending through the sidewall of first shell section 30. Second shell section 32 can include the one or more fastener openings 36 spaced a part along the length of second shell section 32 and aligned with fastener 34 located on first shell section 30. Second shell section 32 can then be slid into first shell section 30 until fastener 34 on first shell section 30 is positioned directly over the particular fastener opening 36 on second shell section 32 desired by a user. Fastener 34 can then be pressed and/or locked into the selected fastener opening 36 to lock first and second shell sections 30 and 32 together at the selected length of device 10. Fastener 34 can subsequently be lifted out of the selected opening 36 and device 10 can be adjusted to a different length where fastener 34 is reinserted into a different opening 36 at a new length desired for device 10. According to one exemplary embodiment, fastener 34 can be biased in a downward position such that unless an upward force is applied to fastener 34, it remains depressed into a fastener opening 36.

Turning now to FIGS. 1-8, device 10 according to one exemplary embodiment will be described in greater detail. FIG. 1 shows a front perspective view of device 10 with an outer shell 12 comprising a first shell section 30 and a second shell section 32 connected together at a selected length by means of fastener 34 and fastener openings 36. Outer shell 12 includes a door 22 comprising first and second door panels 24, where each door panel 24 can be connected to the remainder of the outer shell 12 by a hinged connection. Door panels 24 are configured to open in opposing directions in order to allow access to the interior of device 10. The door panels 24 are securable together by means of latches 26 provided near each end of outer shell 12. As shown, both first shell section 30 and second shell section 32 include a latch 26 to keep door 22 fully closed along the length of device 10. As further shown in FIG. 1, the interior sidewall 16 of shell 12 includes grooved section 20 with a plurality of grooves 40 which can be sized for generally receiving different types of medical circuitry. According to the particular embodiment shown in FIGS. 1-8, device 10 has a diameter of approximately 5 inches and grooved section 20 contains two grooves 40 with diameters of approximately 0.5 inches and two grooves 40 with diameters of approximately 1.5 inches. However, it is recognized that device 10 can be configured with any suitable diameter greater or less than five inches and a grooved section having more or less than four grooves and diameters greater than or less than 0.5 and 1.5 inches.

FIG. 2 shows a rear view of device 10 and illustrates the positioning of securement means 28 configured as quick release clamps according to one exemplary embodiment. As illustrated, each shell section 30 and 32 can have a quick release clamp 28 attached to exterior sidewall 14 adjacent to the ends of outer shell 12. Positioning quick release clamps 28 near the ends of each shell section 30 and 32 can allow second shell section 32 to more fully slide within first shell section 30; however, it is recognized that quick release clamps 28 can be positioned anywhere along the length of each shell section 30 and 32 in various embodiments of the present invention. As also illustrated in FIG. 2, quick release clamps 28 can be attached to exterior sidewall 14 near the lower portion of outer shell 12 in order to allow device 10 to be secured to a hospital bed frame or other object such that grooved section 20 will be orientated in a generally horizontal manner. This arrangement can assist in preventing the medical circuitry from falling out of the grooves 40 located on the interior of device 10.

FIG. 3 shows device 10 with door 22 placed in an open position to allow access to the interior of device 10 in accordance with one exemplary embodiment. As illustrated, both door panels 24 are pivoted along their hinged connection in opposing directions to show the interior sidewall 16 of device 10. As further illustrated, grooved section 20 can be positioned along interior sidewall 16 such that a portion of grooved section 20 is located along the lower portion of interior sidewall 16 and a portion of grooved section 20 is located on the bottom door panel 24. In order to allow the bottom door panel 24 to pivot in the open position about its hinged connection, the hinged connection can extend through grooved section 20 along one of its grooves according to one exemplary embodiment. It is also recognized, however, that grooved section 20 can be positioned in any desired location of interior sidewall 16 of outer shell 12 in various embodiments of the present invention.

FIG. 4 shows a front elevation view of device 10 once door 22 (and door panels 24) have been closed and secured together by latches 26. As shown, first latch portion 26a can be secured to second latch portion 26b in order to keep door 22 secured and maintain device 10 in its closed configuration.

FIG. 5 shows a top view of device 10 illustrating the locations of fastener 34 and fastener openings 36 according to one exemplary embodiment. As illustrated, fastener openings 36 can be spaced apart along the length of second shell section 32 and generally aligned with the position of fastener 34. As also illustrated in FIG. 5, fastener 34 and the corresponding fastener openings 36 can be positioned on outer shell 12 at location other than door 22 and away from door 22 so as to not prevent or obstruct door 22 from opening along its hinged axis according to one exemplary embodiment.

FIG. 6 shows device 10 with medical circuitry 38 secured within the interior of device 10 according to one exemplary embodiment. As illustrated, medical circuitry 38 is positioned in grooved section 20 on interior sidewall 16 of outer shell 12 and contained within the grooves provided in grooved section 20. According to the particular embodiment shown in FIG. 6, medical circuitry can comprise an EKG cord 38a, a pulse oximetry cord 38b, an inspiratory anesthesia tube 38c and an expiratory anesthesia tube 38d. Each component of the medical circuitry 38a-38d can be selectively positioned within one of the grooves comprising grooved section 20. In addition, each groove comprising grooved section 20 can be specifically sized and dimensioned according to the diameter of the specific medical circuitry 38 in certain embodiments of the present invention. For example, EKG cords 38a and pulse oximetry cords 38b generally have a diameter of approximately 0.5 inches. As a result, the grooves in grooved section 20 designed to hold cords 38a and 38b can have a width of approximately 0.5 inches in order to adequately hold and secure cords 38a and 38b. Similarly, inspiratory and expiratory tubes 38c and 38d generally have a diameter of approximately 1.5 inches. As a result, the grooves in grooved section 20 corresponding to tubes 38c and 38d can have a width of approximately 1.5 inches in order to adequately hold and secure tubes 38c and 38d.

FIG. 7 shows device 10 with door 22 in an open position to show interior sidewall 16 of outer shell 12 and grooved section 20 according to an exemplary embodiment. As illustrated in FIG. 7, grooved section 20 can include a plurality of grooves 40 extending along the length of device 10 and interior sidewall 16 of outer shell 12. FIG. 7 illustrates grooved section 20 with four individual grooves 40, which is shown in greater detail in the enlarged schematic view illustrated in FIG. 13. Each groove 40 can be specifically sized and configured to hold a specific type of medical circuitry 38 in certain embodiments of the present invention; however, in it is also recognized that grooves 40 can be generally sized to accommodate several different types of medical circuitry in alternative embodiments. For example, FIG. 13 illustrates a schematic view of grooved section 20 according to one exemplary embodiment where grooved section 20 includes a first groove 40a having approximately a 0.5 inch width to accommodate an EKG cord 38a, a second groove 40b having approximately a 0.5 inch width to accommodate a pulse oximetry cord 38b, a third groove 40c having approximately a 1.5 inch width to accommodate an inspiratory anesthesia tube 38c, and a fourth groove 40d having approximately a 1.5 inch width to accommodate an expiratory anesthesia tube 38d.

FIG. 8 shows a side view of device 10 according to one exemplary embodiment. FIG. 8 best illustrates the positioning of grooved section 20 along the interior sidewall 16 of outer shell 12. As shown, the lower plane 42 of grooved section 20 can generally conform to the shape and contour of interior sidewall 16 and outer shell 12. In addition, the upper plane 44 of grooved section 20 can extend generally horizontally along the width of device 10 and outer shell 12 so that medical circuitry 38 can be adequately secured within each groove 40 when device 10 is in use. In alternative embodiments, the upper plane of grooved section 20 can have a more arcuate configuration that more generally conforms to the shape of interior sidewall 16 in order to reduce the thickness of grooved section 20. As also illustrated in FIG. 8 (and FIG. 14), grooves 40 comprising grooved section 20 can have different widths in order to accommodate different types of medical circuitry 38 with different diameters. According to the embodiment illustrated in FIGS. 8 and 14, grooved section 20 includes two smaller grooves 40a and 40b sized to adequately hold EKG and pulse oximetry cords 38a and 38b and two larger grooves 40c and 40d sized to adequately hold inspiratory and expiratory anesthesia tubing 38c and 38d. Grooved section 20 can also include more or less grooves 40, each having the same or differing widths to accommodate different types of medical circuitry in various embodiments of the present invention.

FIGS. 9 and 10 show an alternative embodiment of the present invention where device 10 includes securement means 28 configured as elongated rods or bars connected to the rear portion of outer shell 12. Each elongated rod 28 can be received by a clamp or other type of receiving component attached to a hospital bed frame in order to be secured to the hospital bed. Such clamps/receiving components are commonly used in the hospital industry for securing various devices and equipment to standard hospital bed frames. As shown, elongated rods 28 can be attached to exterior sidewall 14 along a lower portion of outer shell 12. According to the embodiment shown in FIGS. 9 and 10, elongated rods 28 can be attached to exterior sidewall 14 near the ends of outer shell 12, or alternatively, elongated rods 28 can be positioned anywhere along the length of outer shell 12 in alternative embodiments. Elongated rods 28 can also be orientated in the general vertical direction with a slightly angled configuration that can allow device 10 to be properly positioned on a hospital bed frame and allow grooved section 20 to be orientated generally horizontally when device 10 is secured to the hospital bed frame.

According to one exemplary embodiment, elongated rods 28 do not extend above the upper plan of device 10 in order to prevent the rods 28 from accidentally damaging surgical drapes or other items placed over device 10 when it is attached to a bed frame. In addition, elongated rods 28 can extend below the lower plane of device 10 in order to allow the rods 28 to easily slide into the receiving components of the bed frame without obstruction from the outer shell 12 of device 10.

According to the embodiment illustrated in FIGS. 9 and 10, device 10 can be utilized by sliding elongated rods 28 through the receiving components attached to the surgical or hospital bed frame until device 10 is positioned at the desired height relative to the hospital or surgical bed. Once device 10 is at the desired height, the receiving components can be tightened and device 10 can remain secured in place.

FIGS. 11A and 11B show an embodiment of device 10 where grooved section 20 is configured as a removable mold that can be selectively positioned the interior of outer shell 12. As shown in FIG. 11A, device 10 is configured as described above with an outer shell 12 (which can be constructed from first and second shell sections 30 and 32)

having an exterior sidewall 14 and an interior sidewall 16, a door 22 selectively openable to allow access to the interior sidewall 16 and securement means 28 to secure device 10 to a hospital or surgical bed frame or other object. However, in the embodiment shown, grooved section 20 is not defined into interior sidewall 16, but rather, grooved section 20 is configured as a separate mold that can be inserted into the interior of device 10 and along interior sidewall 16, as shown in FIG. 11B. According to such an embodiment, grooved section 20 can include a lower end 42 that generally conforms to the shape of interior sidewall 16 and an upper end 44 that contains one or more grooves 40 defined therein. Upper end 44 of grooved section 20 can include any suitable number of grooves 40 (such as grooves 40a-40d illustrated in FIG. 11B), each of which can be dimensioned with a desired width to accommodate different medical circuitry.

FIG. 12 shows yet another alternative embodiment of device 10 that includes a reinforcing band 46 secured around exterior sidewall 14 of outer shell 12 in order to provide greater rigidity and structural integrity to device 10. Reinforcing bands 46 can be positioned along the ends of outer shell 12 and can comprise a thickened sidewall section that strengthens the ends of device 10.

Device 10 can be constructed from any number of different desired materials, including but not limited to stainless steel, metal, plastic, rubber, silicone, polymer-based materials or any combination thereof. For example, according to one embodiment, outer shell 12 can be constructed from a stainless steel or other metal material in order to allow device 10 to be effectively cleaned and decontaminated for reuse, while removable grooved section 20 can be constructed from a polymer- or plastic-based material, which can be disposed of after use. Various other constructions and usage of materials can also be suitably used in various embodiments of the present invention.

From the foregoing, it will be seen that this invention is one well adapted to attain all the ends and objects hereinabove set forth together with other advantages which are obvious and which are inherent to the structure. It will be understood that certain features and sub combinations are of utility and may be employed without reference to other features and sub combinations. This is contemplated by and is within the scope of the claims. Since many possible embodiments of the invention may be made without departing from the scope thereof, it is also to be understood that all matters herein set forth or shown in the accompanying drawings are to be interpreted as illustrative and not limiting.

The constructions described above and illustrated in the drawings are presented by way of example only and are not intended to limit the concepts and principles of the present invention. Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "having" and "including" and similar terms as used in the foregoing specification are used in the sense of "optional" or "may include" and not as "required". Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A medical circuit protector device comprising:
an elongated hollow cylindrical tube having an exterior sidewall and an interior sidewall;
an opening defined through each end of said elongated hollow cylindrical tube; at least one latch provided on said exterior sidewall,
said latch configured for allowing said elongated hollow cylindrical tube to be selectively opened and closed;
a plurality of circuit grooves provided on said interior sidewall,
said plurality of circuit grooves configured for retaining one or more medical circuits within said tube;
and securing means provided on said exterior sidewall, said securing means configured for allowing said medical circuit protector device to be selectively secured to an object;
wherein said elongated hollow cylindrical tube comprises a first shell section and a second shell section, said second shell section being slidably receivable within said first shell section for selectively adjusting an overall length of said medical circuit protector device;
wherein elongated hollow cylindrical tube includes a first door and a second door, said first and said second doors connected to said elongate hollow cylindrical tube along a respective hinge line;
further comprising a removable circuit groove mold configured for being inserted into said elongated hollow cylindrical tube and against said interior sidewall, said removable circuit groove mold containing said plurality of circuit grooves;
wherein said plurality of circuit grooves include a pair of primary grooves and a pair of secondary grooves, said primary grooves having a diameter greater than a diameter of said secondary grooves.

2. The medical circuit protector device of claim 1 wherein said second shell section includes an exterior diameter less than an interior diameter of said first shell section for allowing said first shell section to slidably receive said second shell section.

3. The medical circuit protector device of claim 2, wherein said second shell section includes a plurality of fastener openings defined into said exterior sidewall of said elongated hollow cylindrical tube and spaced apart along a length of said second shell section, said fastener openings configured for receiving a fastener provided on said first shell section to selectively secure said first shell section to said second shell section at a desired overall length of said medical circuit protector device.

4. The medical circuit protector device of claim 1, wherein said first and said second doors are selectively openable to allow access to an interior of said elongate hollow cylindrical tube.

5. The medical circuit protector device of claim 4, wherein said at least one latch is configured for securing said first door and said second door in a closed position for substantially enclosed said exterior sidewall of said elongated hollow cylindrical tube.

6. The medical circuit protector device of claim 1, wherein said pair of primary grooves are sized to receive an inspiratory anesthesia circuit tubing and an expiratory anesthesia circuit tubing.

7. The medical circuit protector device of claim 1, wherein said plurality of circuit grooves are located at a lower portion of said elongated hollow cylindrical tube.

8. The medical circuit protector device of claim 1, wherein said securing means are provided on a lower rear section of said exterior sidewall of said elongated hollow cylindrical tube.

9. The medical circuit protector device of claim 1, wherein said securing means comprise a pair of clamps.

10. The medical circuit protector device of claim 9, wherein each said clamp is positioned adjacent to an end of said elongated hollow cylindrical tube.

11. The medical circuit protector device of claim 1, wherein said securing means comprise a pair of elongate rods extending in a perpendicular direction from an axis of said elongated hollow cylindrical tube.

12. The medical circuit protector device of claim 1, further comprising a pair of reinforcement bands provided around said exterior sidewall on each end of said elongated hollow cylindrical tube.

13. The medical circuit protector device of claim 1, where the object comprises a medical bed frame.

14. The medical circuit protector device of claim 1, where the plurality of circuit grooves include at least two grooves of at least 1.5 inch diameter for holding inspiratory and expiratory anesthetic circuit tubing.

\* \* \* \* \*